United States Patent [19]

Gyurik et al.

[11] 4,025,638
[45] May 24, 1977

[54] METHODS AND COMPOSITIONS USING 5-CYCLOALKYLTHIO- AND OXY-2-CARBALKOXY-AMINOBENZIMIDAZOLE

[75] Inventors: Robert J. Gyurik, Downingtown; William D. Kingsbury, West Chester, both of Pa.

[73] Assignee: SmithKline Corporation, Philadelphia, Pa.

[22] Filed: Feb. 2, 1976

[21] Appl. No.: 654,269

Related U.S. Application Data

[60] Division of Ser. No. 557,207, March 10, 1975, which is a continuation-in-part of Ser. No. 364,841, May 29, 1973, abandoned.

[52] U.S. Cl. .................................................. 424/273

[51] Int. Cl.² ........................................ A61K 31/415
[58] Field of Search ................................... 424/273

[56] References Cited
UNITED STATES PATENTS 3,574,845  4/1971  Actor et al. .................... 260/309.2

FOREIGN PATENTS OR APPLICATIONS 809,234  6/1974  Belgium ........................ 260/309.2

*Primary Examiner*—Sam Rosen
*Attorney, Agent, or Firm*—William H. Edgerton; Alan D. Lourie; Richard D. Foggio

[57] ABSTRACT

New anthelmintic compositions and methods of use are described utilizing 5-cycloalkylthio and oxy-2-carbalkoxyaminobenzimidazoles as active ingredients.

11 Claims, No Drawings

METHODS AND COMPOSITIONS USING 5-CYCLOALKYLTHIO- AND OXY-2-CARBALKOXY-AMINOBENZIMIDAZOLE

This application is a division of our copending application Ser. No. 557,207, filed Mar. 10, 1975 which is a continuation-in-part of Ser. No. 364,841 filed May 29, 1973, now abandoned.

This invention comprises as new compounds, 5-cycloalkylthio- and oxy-2-carbalkoxyaminobenzimidazoles, together with novel methods and compositions for producing anthelmintic activity using these benzimidazoles. The compounds of this invention are distinguished by having a cycloalkylthio or oxy moiety at position 5 of the benzimidazole nucleus.

Prior patents have demonstrated that certain benz-substituted and unsubstituted 2-carbalkoxyaminobenzimidazoles have anthelmintic activity (See U.S. Pat. Nos. 3,574,845 and 3,682,952). Among the ring substituents in the 3,682,952 patent in column 1, line 40, the closest to the novel substituents in the compounds of this invention are "lower alkyl thio" or "lower alkoxy" of this reference. No cycloalkyl containing nuclear substituents are disclosed in the structures.

We have found that 2-carbalkoxyaminobenzimidazole compounds having a cycloalkyl thio or oxy substituent at the 5-position rather than an open chain alkyl thio or alkoxy group are extremely active, especially the thio compounds. By "cycloalkyl" we mean a 3 to 8 carbon member alicyclic group containing a 3–6 member ring structure such as cyclopropyl, cyclohexyl, cyclopentyl, cyclopropylmethyl, cyclohexylmethyl, cyclohexylethyl or cylopentylmethyl.

Representative compounds illustrating the new 5-cycloalkylthio- or oxy-2-carbalkoxyaminobenzimidazoles of this invention are the following:

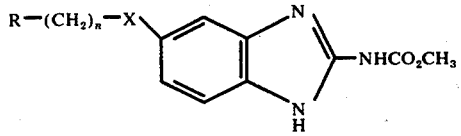

in which R is a cycloalkyl ring of from 3 to 6 members, $n$ is an integer of from 0–5 with $R(CH_2)_n$ having from 3–8 carbons, preferably the cyclic moiety has 3, 5 or 6 members. The alkylene chain if present has one member, i.e. methylene, for convenience. The cyclohexylthio and cyclopentylthio containing compounds are exceptionally active.

Other carbalkoxyamino groups can be substituted for the 2-carbomethoxyamino of Formula I however with little advantage over the simple carbomethoxy compounds. See for example U.S. Pat. No. 3,682,952 in which the alkyl group of the 2-carbalkoxyamino moiety is described as lower alkyl from one to six carbon atoms, cycloalkyl including cycloalkyl containing three to ten carbon atoms, alkenyl straight or branched containing two to ten carbon atoms, alkynyl straight or branched containing from two to ten carbon atoms, phenyl or naphthyl.

The compounds of this invention can be prepared and used by the methods similar to those described herein or in U.S. Pat. No. 3,682,952 using the known mercaptans or phenols as starting materials. The preferable route of synthesis is the reaction of a 4-cycloalkylthio- or oxy-o-phenylenediamine with methyl cyanocarbamate, formed from cyanamide and methyl chloroformate. The formation of the benzimidazole usually is carried out in an aqueous miscible solvent system in the presence of alkali such as an alkali metal hydroxide or carbonate. The solvent systems most useful are acetone, methanol, ethanol, pyridine, dimethylsulfoxide, dimethylacetamide, dimethylformamide and the like. The reaction is carried out at temperatures ranging from room temperature up to the boiling point of the reaction mixture or, if the solvent is high boiling, to steam temperature.

The novelty of the activity of these compounds is demonstrated by the fact that in tests against nematodes in sheep the cyclohexylthio containing congener reduces Haemonchus contortus 99.7% at 15 mg kg orally.

The 5-cycloalkylthio- and oxy-benzimidazoles of Formula I have useful general anthelmintic properties, that is, broad spectrum activity against parasites of warm blooded animals, including both mature and immature parasitic forms. In particular, these compounds have high activity against various helmintic infections of the intestinal tract of economically important animals, coupled with low systemic toxicity to the host animal.

For example, the disclosed compounds are generally effective in clearing mice of worm infections for laboratory purposes, among other: *Syphacia obvelata* and *Aspicularis tetraptera* (mouse pinworm), *Nematospiroides dubius* (mouse hookworm), and the migratory stages of *Ascaris suum*.

Other susceptible helminths include *Toxocara canis*, found in naturally infested dogs. Also, parasitic to this host are *Ancylostoma canium*, *Trichuris vulpis* (whipworm), and *Physalaptera spp*.

These compounds are efficacious against parasites of pigs, such as the migratory stages of *Ascaris suum*, thus preventing the development of verminous pneumonia.

Compounds of Formula I are most efficacious against parasitic gastroenteritis in sheep, such as *Haemonchus contortus*, *Ostertagia spp.*, *Trichostrongylus spp.*, *Nematodirus spp.*, *Trichuris ovis*, *Cooperia spp.*, and *Strongyloides papillosus*. *Bunostomum trigonocephalum* and *Oesophagostomum spp.*, are other important parasites of sheep.

Animals of low weight are treated with unit doses ranging no higher than a few milligrams; whereas animals of high body weight, such as ruminants, require proportionately larger unit doses ranging up to several grams. Preferably, a single dose is administered daily for each animal species based on the weight of that species.

The amount of ingredient administered will depend on the weight of the host, but will usually be between about 1 mg./kg. and 100 mg./kg. of body weight daily In nematode infections in sheep from about 1–25 mg./kg. will clear substantially all the worms from the intestinal tract. Essentially the compounds of Formula I have at least the same spectrum as does the prior art parbendazole but the preferred compounds are more active, i.e. active at lower doses of active ingredient.

In practice, an active compound of the structure of Formula I is usually formulated with a non-toxic carrier therefor to give anthelmintic compositions of this invention. The carrier may be an orally ingestible container for the active ingredient, for example, a hard or soft gelatin capsule; or it may be a pharmaceutically acceptable diluent of excipient of the kind normally used in the production of medicaments, ready for use, for example maize starch, terra alba, lactose, sucrose, calcium phosphate, gelatin, talcum, stearic acid, magnesium stearate, dextrin, agar, pectin or acacia.

Exemplary of liquid carriers are peanut oil, olive oil, sesame oil, and water. Similarly, the carrier or diluent may include a time delay material such as glyceryl monostearate or glyceryl distearate alone or with a wax.

A wide variety of pharmaceutical forms can be employed. Thus, if a solid carrier is used, the preparation can be tableted, placed in a hard geletin capsule, or compounded in the form of a troche or lozenge. The amount of solid carrier will vary widely but preferably will be from about 25 mg. to about 3 mg. If a liquid carrier is used, the preparation may be in the form of a soft gelatin capsule, placed in an ampule or in liquid suspension.

The compositions are most often made up in a form suitable for oral administration and may therefore take the form of a liquid, for example, an emulsion or a solution or suspension in water, oil, such as arachis oil or other liquid.

The compositions are advantageously made up in a dosage unit form adapted for the desired mode of administration. Thus for the preferred oral administration, the dosage unit may take the form of a suspension, tablet, packaged powder, bolus, or encapsulated powder. The quantity of active ingredient in each dosage unit will be such that one or more units are required for each therapeutic administration.

As previously mentioned, the compounds of Formula I have general anthelmintic activity and accordingly a further and most important aspect of this invention provides a method of treating helmintic infections in an animal which comprises administering, usually orally, to the animal in a sufficient nontoxic, but effective, dose an anthelmintic compound falling within the definition of Formula I, generally in the form of a pharmaceutical or veterinary composition as hereinbefore described. The daily dose range commonly used is from about 1 mg./kg. to about 300 mg./kg. preferably about 3 mg./kg.-50 mg./kg. depending on the species of host and regimen used. One dose per day administration is preferred but up to five of the dosage units described above may be used if desired. The daily dose range is therefore identical to the dosage unit range.

Where tableting is used, the resulting tablets may be then coated with methyl methacrylate to form an enteric coating, i.e. a coating which is substantially insoluble in gastric secretion but substantially soluble in intestinal fluids.

The compositions thusly prepared are administered, usually orally, to an infected or susceptible host from 1–5 times daily for curative or prophylactic anthelmintic activity.

The following examples illustrate synthesis which may be employed in formulating the compositions of the invention but are not considered limiting the invention described herebefore.

EXAMPLE 1

| EXAMPLE 1 | |
|---|---|
| Typical Cattle Bolus | |
| 5-cyclohexylthio-2-carbomethoxyamino-benzimidazole | 0.25 grams |
| Calcium phosphate | 2.5 grams |
| Maize starch | 0.54 grams |
| Talcum | 0.14 grams |
| Gum arabic | 0.15 grams |
| Magnesium stearate | 0.5 grams |

The calcium phosphate and the anthelmintic compound are thoroughly mixed, and the mixture reduced to a particle size finer than 60 mesh. About one-half of the starch is added, as an aqueous paste, and the resulting mixture granulated. The granules are passed through a 010 mesh screen and dried at 110°–130° F. for about 8 hours. The dried materials then passed through a No. 16 mesh screen. The guar gum and the balance of the starch are added and the mixture thoroughly blended. Finally, the remainder of the ingredients are added and the entire mass thoroughly mixed and compressed into a bolus. The magnesium stearate, talcum and gum acacia are of a particle size to pass a No. 10 mesh screen.

EXAMPLE 2

| Typical Sheep Drench | Parts by Weight |
|---|---|
| 2-Cyclopropylthio-2-carbomethoxyamino-benzimidazole | 60 |
| Terra Alba English | 35.5 |
| Tragacanth, U.S.P. | 3.0 |
| Sodium Lauryl Sulfate | 1.5 |
| Water | |

The above solid components are thoroughly mixed, giving a water dispersable powder. This powder can be directly admixed with water in concentrations on the order of 10.5 g. of powder to 5 cc. of water.

EXAMPLE 3

| Novel Sheep Drench | |
|---|---|
| 5-Cyclopentyloxy-2-carbomethoxyamino-benzimidazole | 2 grams |
| 0.1N HCl solution | quantum sufficient to make 1 liter |

EXAMPLE 4

A solution of 2.64 g. (0.04 mol) of potassium hydroxide (85%) in 50 ml. of water is added to 2.3 g. (0.02 mol) of cyclohexylmethylthiol (97%) in 20 ml. of ethanol. The resulting mixture is brought to reflux. After 25 minutes, 4.28 g. of 2-nitro-5-chloroacetanilide in 40 ml. of ethanol is added dropwise. The reaction mixture is heated at reflux for 4 hours. Standing overnight gives the desired 2-nitro-2-cyclohexylmethylthioaniline.

A mixture of 3.7 g. (0.015 mol) of the thio compound in 150 ml. of ethanol, 3 ml. (0.035 mol) of concentrated hydrochloric acid with 0.5 g. of 5% palladium-on-charcoal is hydrogenated at 53 lb. hydrogen pressure. The filtrate from the hydrogenation mixture is added dropwise over 45 minutes at 5° C. to a previously reacted carbomethoxycyanamide mixture [2.52 g. (0.06 mol) of cyanamide in 5 ml. of water with 5.87 g. (0.06 mol) of methyl chloroformate in 10 ml. of acetone at 5°–10° C. which had been neutralized with 2.4 g. of sodium hydroxide.] After reaction was complete, the volatile solvent was removed and the mixture heated one hour at 85° C. Water is added to separate 5-cyclohexylmethylthio-2-carbomethoxyaminobenzimidazole.

EXAMPLE 5

Repeating the reaction of Example 1 but using 10.0 g. of cyclohexylethylthiol gives 2-nitro-5-cyclohexylethylthioaniline. The nitro compound is reduced. The reduction mixture is reacted with carbomethoxycyanamide as described to give 5-cyclohexylethylthio-2-carbomethoxyaminobenzimidazole.

Using α-cyclobutylethylthiol gives 5-cyclobutylethylthio-2-carbomethoxyaminobenzimidazole; cyclopentylmethylthiol gives 5-cyclopentylmethylthio-2-carbomethoxyaminobenzimidazole; cyclohexylthiol gives 5-cyclohexylthio-2-carbomethoxyaminobenzimidazole, m.p. 224–230 dec. with gas; immersed at 200° C.; cyclopentylthiol gives 5-cyclopentylthio-2-carbomethoxyaminobenzimidazole.

EXAMPLE 6

A mixture of cyclohexanol (0.03 mol) in 75 ml. of dry dimethylformamide under nitrogen is agitated while 55% sodium hydride (0.03 mol) in oil is added portionwise. When evolution of hydrogen ceases 2-nitro-5-chloroaniline (0.025 mol) is added with stirring. The mixture is warmed at 75°–80° C. for 1 hour then poured onto 6 volumes of ice slurry. The separated product recrystallized from water to give red crystals of the nitroaminobiphenylether. After hydrogenation and reaction with carbomethoxycyanamide as described above the product, 5-cyclohexyloxy-2-carbomethoxyaminobenzimidazole is obtained.

Repeating this procedure with cylopentanol, cyclopentylethanol, and cyclopropylpropanol gives the corresponding benzimidazoles.

EXAMPLE 7

A heated mixture of 7.6 g. of thiourea and 40 ml. of ethanol is mixed with 13.3 g. of cyclopropylmethyl bromide in 5 portions. After an exothermic reaction, the mixture is heated at reflux for 2 hours. The reaction mixture containing the 5-cyclopropylmethylthiouronium bromide is evaporated. The residue is mixed with 150 ml. of aqueous ethanol and 33 g. (5 mole eq.) of 85% potassium hydroxide. The warm solution is then reacted at reflux with 20 g. of 3-chloro-6-nitroacetanilide for 4 hours. The nitroaniline product, m.p. 88.5°–99.5° C., is reduced catalytically under low pressure hydrogen using platinum oxide in toluene-ethanol solution. After separating the catalyst, the reaction liquor is made acid with alcoholic hydrogen chloride to separate 4-cyclopropylmethylthiophenylene diamine dihydrochloride (dec. over 75° C.).

A mixture of the diamine (2.55 g.), 3 g. of pseudo thiourea, 2 equivalents of sodium bicarbonate in 75 ml. of 50% methanol is heated at reflux for 3 hours. After filtering and washing the product, 5-cyclopropylmethylthio-2-carbomethoxyaminobenzimidazole melts gradually at 220.5°–222.5° C. immersed at 200° C.

Using the diamine in the preferred cyanamide reaction described above gives the same end product, 5-cyclopropylmethylthio-2-carbomethoxyaminobenzimidazole.

Repeating this procedure with cyclopropyl bromide gives 5-cyclopropylthio-2-carbomethoxyaminobenzimidazole. Other halides may be used in the same reaction such as cyclobutylethyl bromide, α-cyclopentylpropylchloride and others.

We claim:

1. The method of producing anthelmintic activity in warm blooded animals susceptible to helminthic infections comprising administering orally to said animals an anthelmintically effective but nontoxic quantity of a chemical compound of the structure:

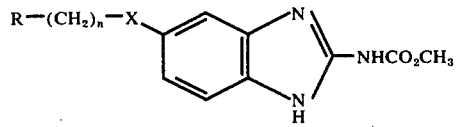

in which R is cycloalkyl of 3–6 carbons, n is an integer of from 0–5 and X is oxy or thio, $R(CH_2)_n$ having 3–8 carbons.

2. The method of claim 1 in which the compound is that in which X is thio.

3. The method of claim 1 in which the compound is that in which X is thio and n is O.

4. The method of claim 2 in which the compound is that in which $R(CH_2)_n$ is cyclohexyl.

5. An anthelmintic composition comprising a carrier and an anthelmintically effective but nontoxic quantity of a compound of the structure:

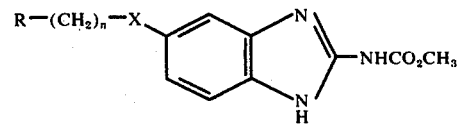

in which R is cycloalkyl of 3–6 carbons, n is an integer of from 0–5 and X is oxy or thio, $R(CH_2)_n$ having 3–8 carbons; said quantity being from about 1–100 mg./kg. per dosage unit.

6. The composition of claim 5 in which the compound is 5-cyclohexylthio-2-carbomethoxyaminobenzimidazole.

7. The composition of claim 5 in which the compound is 5-cyclohexyloxy-2-carbomethoxyaminobenzimidazole.

8. The composition of claim 5 in which the composition is a veterinary drench or bolus.

9. The composition of claim 6 in which the quantity of the compound is from about 1–25 mg./kg. per dosage unit.

10. The method of claim 1 in which the compound is that in which X is oxy.

11. The composition of claim 5 in which the compound is that in which X is oxy.

* * * * *